United States Patent
Koga et al.

(10) Patent No.: US 9,855,201 B2
(45) Date of Patent: *Jan. 2, 2018

(54) VOLATILE OIL FOR COSMETICS

(71) Applicant: NOF Corporation, Shibuya-ku, Tokyo (JP)

(72) Inventors: Nariyoshi Koga, Oita (JP); Tohru Nishikawa, Aichi (JP)

(73) Assignee: NOF Corporation, Tokyo (JP)

( * ) Notice: Subject to any disclaimer, the term of this patent is extended or adjusted under 35 U.S.C. 154(b) by 124 days.

This patent is subject to a terminal disclaimer.

(21) Appl. No.: 14/404,260

(22) PCT Filed: Jun. 18, 2013

(86) PCT No.: PCT/JP2013/066766
§ 371 (c)(1),
(2) Date: Nov. 26, 2014

(87) PCT Pub. No.: WO2014/002837
PCT Pub. Date: Jan. 3, 2014

(65) Prior Publication Data
US 2015/0150765 A1  Jun. 4, 2015

(30) Foreign Application Priority Data

Jun. 28, 2012 (JP) .................. 2012-146171
Sep. 24, 2012 (JP) .................. 2012-210141

(51) Int. Cl.
| C10M 105/04 | (2006.01) |
| A61K 8/31 | (2006.01) |
| A61Q 19/00 | (2006.01) |
| A61Q 5/00 | (2006.01) |
| A61Q 5/06 | (2006.01) |
| A61Q 5/12 | (2006.01) |
| A61Q 1/02 | (2006.01) |
| A61Q 5/02 | (2006.01) |
| A61Q 19/10 | (2006.01) |

(52) U.S. Cl.
CPC .............. *A61K 8/31* (2013.01); *A61Q 5/00* (2013.01); *A61Q 5/06* (2013.01); *A61Q 19/00* (2013.01); *A61Q 19/007* (2013.01); *A61K 2800/10* (2013.01); *A61K 2800/20* (2013.01); *A61Q 1/02* (2013.01); *A61Q 5/02* (2013.01); *A61Q 5/12* (2013.01); *A61Q 19/10* (2013.01)

(58) Field of Classification Search
CPC ........ C10M 105/04; C10M 2203/0206; C10M 2203/022
USPC ...................... 585/1, 16, 250, 255
See application file for complete search history.

(56) References Cited

U.S. PATENT DOCUMENTS

| 4,061,780 | A | 12/1977 | Yoshida et al. |
| 8,821,842 | B2* | 9/2014 | Lange .............. A61K 8/046 424/70.11 |
| 8,992,953 | B2* | 3/2015 | Clavel .............. A61K 8/06 424/401 |
| 2009/0123398 | A1 | 5/2009 | Laba et al. |
| 2010/0143273 | A1* | 6/2010 | Auguste .......... A61K 8/046 424/59 |
| 2011/0165102 | A1* | 7/2011 | Arditty ............ A61Q 1/10 424/70.7 |
| 2011/0217253 | A1* | 9/2011 | Arnaud ........... A61K 8/06 424/63 |
| 2012/0027702 | A1* | 2/2012 | Bernoud ......... A61K 8/31 424/59 |
| 2012/0308506 | A1* | 12/2012 | Oku ................ A61K 8/31 424/70.122 |
| 2014/0079656 | A1* | 3/2014 | Clavel ............ A61K 8/06 424/63 |
| 2015/0005550 | A1* | 1/2015 | Koga ............. A61K 8/31 585/16 |

FOREIGN PATENT DOCUMENTS

| CA | 2 862 593 A1 | 7/2014 |
| JP | H 06-157276 A | 6/1994 |
| JP | 2002-068928 A | 3/2002 |
| JP | 2008-544951 A | 12/2008 |
| JP | 2009-286752 A | 12/2009 |
| JP | 2011-503192 A | 1/2011 |
| JP | 2012-001670 A | 1/2012 |
| JP | 2013-177349 A | 9/2013 |
| WO | WO 2013/118533 A1 | 8/2013 |

OTHER PUBLICATIONS

Isohexadecane MSDS (online), Version 1, INEOS, http://freedownloadb.com/pdf/material-safety-data-shee-wordpresscom-get-a-free-blog-here-21011494.html, pp. 1-5 (Feb. 21, 2007).
Fancol IH, (online), Elementis Specialities, http://freedownloadb.com/pds/fanco-l-ih-esp-home-spa-products-cosmetic-raw-materials-49552863.html, pp. 1-2 (Nov. 11, 2010).
Hiroshi Hirota, Keshohin-yo Yushi no Kagaku, $2^{nd}$ print, Fragrance Journal Sha, pp. 54-56 (Apr. 10, 2001) with English Translation.

* cited by examiner

*Primary Examiner* — Ellen McAvoy
(74) *Attorney, Agent, or Firm* — Muncy, Geissler, Olds & Lowe, P.C.

(57) ABSTRACT

Provided is a volatile oil for cosmetics, which has excellent volatility, hair care properties and skin care properties. The volatile oil for cosmetics according to the present invention comprises a paraffin mixture, wherein the paraffin mixture contains an isoparaffin having 12 to 16 carbon atoms, has a boiling point ranging from 185 to 215° C. and has a 2,2,4,6,6-pentamethylheptane content of less than 10 mass %. The volatile oil for cosmetics according to the present invention can be used for, for example, a hair cosmetic and an external preparation for the skin.

4 Claims, No Drawings

VOLATILE OIL FOR COSMETICS

BACKGROUND OF THE INVENTION

Technical Field

The present invention relates to a volatile oil for cosmetics having excellent volatility, hair care properties, and skin care properties, and relates to a volatile, oil that may be used for, for example, hair cosmetics and external preparations for skin.

Background Art

As hydrocarbons that have been conventionally used as volatile oils, hydrocarbons having a carbon number of 6 to 12 are known, including, for example, n-hexane, isohexane, cyclohexane, n-octane, isooctane, n-nonane, n-decane, and isododecane. Unfortunately, there is a problem in that those volatile oils lack safety since their flash point is low at 50° C. or below. When these volatile oils are used for oils contained in cosmetics or cleansers for hair and skin, there are problems in that they are too stimulative to skin including scalp and mucous membrane, and they are so volatile that moisture is likely to evaporate from the surface layer of a living body.

Also, in case of hydrocarbons having a carbon number of 15 or more including, for example, n-pentadecane and isohexadecane, improvements in performance such as higher flash points and less stimulation to skin and mucous membranes are expected since they have higher molecular weights. However, they have a problem in that, as their volatility is lower, oil is likely to linger, leaving poor texture when applied to hair or skin.

Based on this background, Patent Literature 1, for example, discloses a non-silicone composition in which a hydrocarbon having a carbon number of 12 to 14, a hydrocarbon having a carbon number of 13 to 16, and a non-volatile hydrocarbon are combined, as a volatile oil having excellent volatility, high flash point as well as safety oil a human body. Moreover, in the field of cosmetics, Patent Literature 2, for example, discloses hair cosmetics in which cyclic silicones such as cyclomethicone are used as a volatile component (see claim 1, for example, in the same Literature). Also, Patent Literature 3 discloses external preparations for skin in which cyclic silicones such as cyclomethicone are used as a volatile component (see paragraphs [0039] and [0040] in the same Literature).

CITATION LIST

Patent Literature

[PRL 1] Japanese Unexamined Patent Application Publication (Translation of PCT Application) No. 2011-503192
[PTL 2] Japanese Unexamined Patent Application Publication No. 2009-286752
[PTL 3] Japanese Unexamined Patent Application Publication No. H6-157276

SUMMARY OF THE INVENTION

Technical Problem

However, since the non-silicone composition contains 2,2,4,6,6-pentamethylheptane in the method of Patent Literature 1, there is a problem in that it has a strong odor. There is also a problem in that it provides a squeaky sensation when applied to hair and it makes skin whitish and dry when applied thereon, providing poor texture, so that it is not preferable for cosmetics or cleaning oils.

On the other hand, although volatility is excellent in the methods of Patent Literature 2 and Patent Literature 3, its safety for human bodies and the environment is a concern, so that there is a problem in that it is not preferable for cosmetics or cleaning oils on skin including hair.

Accordingly, an object of the present invention is to provide a volatile oil for cosmetics having excellent volatility, hair care properties, and skin care properties, and to provide a volatile oil that may be used for, for example, hair cosmetics and external preparations for skin.

Solution to Problem

The inventors found that the above object may be met when a carbon number of paraffin, a boiling point range, and the content of 2,2,4,6,6-pentamethylheptane are provided within a certain range in a paraffin mixture.

Specifically, the present, invention relates to a volatile oil for cosmetics including a paraffin mixture that contains isoparaffin having a carbon number of 12 to 16, has a boiling point range of 185° C. to 215° C., and contains 2,2,4,6,6-pentamethylheptane at less than 10 mass %.

"Use for cosmetics" in the present, invention includes use for hair cosmetics and use for external preparations for skin. In other words, the volatile oil for cosmetics of the present invention includes the following (A) and (B) aspects.

(A) A volatile oil for hair cosmetics including a paraffin mixture that contains isoparaffin having a carbon number of 12 to 16, has a boiling point range of 185° C. to 215° C., and contains 2,2,4,6,6-pentamethylheptane at less than 10 mass %.

(B) A volatile oil for external preparations for skin including a paraffin mixture that contains isoparaffin having a carbon number of 12 to 16, has a boiling point range of 185° C. to 215° C., and contains 2,2,4,6,6-pentamethylheptane at less than 10 mass %.

"Hair cosmetics" in the present invention are cosmetics, cleansers, and pharmaceutical preparations for hair and scalp, including, for example, an aerosol hair spray, a pump type hair spray, a foam type hair spray, a hair mist setting lotion, a hair styling product, hair oil, shampoo, conditioner, perm solution, and hair treatment.

Additionally, "external preparations for skin" of the present invention are external preparations for skin, except for the above-noted hair cosmetics. The external preparations for skin include cosmetics and pharmaceutical preparations for skin such as lotion, cleanser, milky lotion, cream, ointment, pack, hair tonic, and foundation for skin.

Advantageous Effects of Invention

The volatile oil for cosmetics of the present invention has excellent volatility and high flash point, so that the oil is safe when be handled as well as safe on human bodies and the environment and has excellent various types of hair care properties when applied to hair and excellent various types of skin care properties when applied to skin. Accordingly, the volatile oil for cosmetics of the present invention is useful as a material for cosmetics, cleaning oils, and pharmaceutical preparations for hair and skin. The volatile oil is useful as a substitute for cyclic silicones such as cyclopentasiloxane.

DESCRIPTION OF THE EMBODIMENTS

Embodiments of the present invention will be explained below.

The volatile oil for cosmetics of the present invention includes a paraffin (saturated hydrocarbon) mixture that contains isoparaffin (branched saturated hydrocarbon) having a carbon number of 12 to 16, and may also contain a straight chain saturated hydrocarbon having a carbon number of 12 to 16.

Also, the volatile oil for cosmetics of the present invention may contain a hydrocarbon other than a saturated hydrocarbon having a carbon number of 12 to 16, for example, a cyclic saturated hydrocarbon and an unsaturated hydrocarbon, as long as it would not be contrary to the object of the present invention.

The paraffin mixture in the volatile oil for cosmetics of the present invention has a boiling point range of 185° C. to 215° C., or preferably 186° C. to 210° C. When the paraffin mixture has a boiling point of below 185° C., a flash point becomes low, so that it is not preferable in terms of safety. When the boiling point exceeds 215° C., its volatility decreases and oil is likely to linger, thus leaving poor texture when applied to hair or skin. The boiling point may be measured by a determination of distillation characteristics in accordance with JIS K2254.

It is noted that it is preferable in terms of safety and odor that the paraffin mixture of the present invention has a flash point within the range of 61° C. to 70° C., or preferably within the range of 62° C. to 67° C., in a closed cup method in accordance with JIS K2265. For example, a commercial product, isododecane (in which the content of 2,2,4,6,6-pentamethylheptane is 95 mass % or more), has a boiling point of 177° C., and its flash point is low at about 48° C., which requires caution around flame. It also has a strong odor. On the other hand, when its flash point exceeds 70° C., it may deteriorate its drying property, providing a heavy feeling.

The paraffin mixture of the present invention contains 2,2,4,6,6-pentamethylheptane (hereinafter also referred to as "isododecane") at less than 10 mass %, preferably less than 8 mass %, or more preferably less than 5 mass %. When the content of isododecane in the mixture is 10 mass % or more, its boiling point decreases, which is not preferable in terms of safety. Also, odor becomes strong and the texture for hair or skin deteriorates, thereby limiting use as a material for cosmetics and the like.

The paraffin mixture of the present invention may be produced by steps including, for example, the following steps 1 to 4.

Step 1) providing a polybutene mixture having a carbon number of 16 or less by removing an unreacted component and a polymer having a carbon number of 20 or more from a polymerization reaction system of isobutylene and normal butene;

Step 2) providing a paraffin mixture having a carbon number of 16 or less by hydrogenating the polybutene mixture having a carbon number of 16 or less that is provided in step 1;

Step 3) treating the paraffin mixture having a carbon number of 16 or less that is provided in step 2 with an adsorbent so as to have an iron content of 10 ppm or less; and Step 4) distilling the paraffin mixture having a carbon number of 16 or less that is treated with an adsorbent in step 3 by 15 mass % or more with respect to a charged quantity by vacuum distillation.

The above-noted steps 1 to 4 will be explained sequentially.

First, the polymerization reaction system of isobutylene and normal butene for use in step 1 may be obtained by a conventional method, for example, in cationic polymerization using a catalyst, from a mixed gas of isobutylene and normal butene as a C4 fraction in fractions obtained from cracking naphtha. Thus, the polymerization reaction system of isobutylene and normal butene contains a polybutene mixture (which is the mixture of a copolymer of isobutylene and normal butene, isobutylene (co)polymer, and normal butene polymer, and is the mixture of unsaturated hydrocarbon having a carbon number of 8 or more), an unreacted component (isobutylene, normal butene, etc. contained in the mixed gas), a catalyst, and so forth.

Normal butene has an isomer of 1-butene, cis-2-butene, and trans-2-butene therein. As for the composition of the mixed gas so as to provide the copolymer of isobutylene and normal butene, it is preferable that isobutylene is 15 to 80 mass %, 1-butene is 10 to 40 mass %, and cis-2-butene and trans-2-butene are total 10 to 60 mass %; it is more preferable that isobutylene is 15 to 70 mass %, 1-butene is 15 to 40 mass %, and cis-2-butene and trans-2-butene are total 15 to 60 mass %; it is particularly preferable that isobutylene is 15 to 60 mass %, 1-butene is 15 to 40 mass %, and cis-2-butene and trans-2-butene are total 15 to 40 mass % it is further preferable that isobutylene is 20 to 50 mass %, 1-butene is 18 to 25 mass %, and cis-2butene and trans-2-butene are total 18 to 40 mass % or it is more preferable that isobutylene is 20 to 33 mass %, 1-butene is 18 to 25 mass %, and cis-2-butene and trans-2-butene are total 18 to 25 mass %. Moreover, the mixed gas may contain a component that does not contribute to copolymerization reaction, such as isobutane and butane.

The catalyst in use for cationic polymerization includes, for example, aluminum chloride, acidic ion-exchange resin, sulfuric acid, boron fluoride, and the complex thereof. It is also possible to control polymerization reaction by adding a base to the catalyst. The polymerization reaction is normally carried out at 40° C. to 120° C.

As noted above, the polymerization reaction system of isobutylene and normal butene contains a polybutene mixture as a polymerization reactant of isobutylene and normal butene, an unreacted component, and so forth. In step 1, an unreacted component and a polymer having a carbon number of 20 or more are removed from the above-noted polymerization reaction system so as to provide a polybutene mixture having a carbon number of 16 or less. Distillation is preferable as the removal method. The distillation may include, for example, simple distillation, continuous distillation, steam distillation, and thin-film distillation. The distillation may be carried out alone or in combination thereof. There is no particular limitation on the, for example, materials, shapes, and models of apparatuses used for the distillation. The apparatuses include, for example, a distillation column filled with a filling material such as Raschig rings, and a plate distillation column having disc plates. It is also desirable that the distillation column has the theoretical plate number, indicating the separability of the distillation column, of 10 or above. Other conditions such as feed amount to the distillation column, a reflux ratio, and an output amount may be appropriately chosen depending on a distillation apparatus.

In step 2, the polybutene mixture having a carbon number of 16 or less that is provided in step 1 is hydrogenated so as to provide a polybutene hydrogenated product, in other words, a paraffin mixture having a carbon number of 16 or less that contains isoparaffin. The polybutene having a carbon number of 16 or less provided in step 1 has kept double bonds at polymer terminals, so that deterioration of coloring, etc. would occur when stored over a long period. In order to solve this, the polybutene is hydrogenated in step 2 to be a hydrogen-added product. The hydrogenation reaction may be carried out, for example, by using nickel, palladium or the like as a hydrogenation catalyst at the temperature of 180° C. to 230° C. and bringing it into contact with hydrogen under a pressure of 2 MPa to 10 MPa. It is preferable that a degree of hydrogenation so as to provide a paraffin mixture of the present invention be 10 or less in iodine value. A more preferable degree of hydrogenation is 1 or less in iodine value, and a further preferable degree of hydrogenation is 0.1 or less in iodine value. When an iodine value exceeds 10, oxidation with heat and light is likely to accelerate, which often causes odor.

The paraffin mixture having a carbon number of 16 or less provided in step 2 sometimes gets mixed with a trace metal compound contained in the catalyst used for hydrogenation reaction, and a trace metal such as iron that is generated from the corrosion of a reactor due to high acidity of the catalyst. These trace metals cause adverse effect on the odor and storage stability of the paraffin mixture. When particularly iron, among trace metals, is mixed in, odor worsens at the reaction in the following distillation step of providing the paraffin mixture of the present invention, thus causing unpleasant odor. Therefore, in order to control coloring and odor, the paraffin mixture having a carbon number of 16 or less is treated with an adsorbent in step 3.

As the adsorbent, inorganic and organic adsorbents are used. For example, clay, kaolin, talc, calcium carbonate, diatom earth, zeolite, bentonite, acid clay, activated clay, vermiculite, silica gel, molecular sieve, and activated carbon are used. Particularly, activated clay and clay are effective. One or more of these adsorbents may be used. The adsorbent not only physically removes a trace metal and iron from a hydrogenation reaction catalyst but is also effective in removing a slightly decomposed and byproduct low-molecular-weight, oxide caused at high temperature in hydrogenation, and is further effective for the temporal stability of a product after distillation. The particle size of the adsorbent for use is not particularly limited. However, when one kind of adsorbents is used, it is preferable to combine adsorbents having different particle sizes. The combination of adsorbents having different particle sizes may be properly selected based on the dispersion of pressure inside the column filled with the adsorbents and efficient treatments. When two or more kinds of adsorbents are used, it is more effective in manufacturing to fill the adsorbent having the relatively smallest particle size by 50 to 80 volume % of a column volume.

The paraffin mixture treated with an adsorbent in step 3 contains isododecane having a low flash point and unpleasant odor. Thus, in step 4, the paraffin mixture having a carbon number of 16 or less that is treated with an adsorbent in step 3 is subjected to vacuum distillation. With respect to a charged quantity before this vacuum distillation, 15 mass % or more, preferably 25 mass % or more, is distilled. It is noted that in order to prevent a flash point of the paraffin mixture from decreasing, a distillation rate is preferably 40 mass % or less, or more preferably 35 mass % or less with respect to a charged quantity before the vacuum distillation.

For the distillation in vacuum distillation, the distillation method and distillation apparatus described in the above-noted step 1 may be applied. As distillation conditions, liquid temperature inside a chamber is 50° C. to 180° C. or preferably 100° C. to 180° C., and pressure inside the chamber is 0.5 kPa to 80 kPa or preferably 5 kPa to 80 kPa. By the distillation in this step, isododecane and other low boiling point substances (such as a saturated hydrocarbon having a carbon number of 8) contained in the paraffin mixture may be distilled.

After the steps including the above-noted steps 1 to 4, the paraffin mixture containing isoparaffin having a carbon number of 12 to 16 may be produced.

The volatile oil for cosmetics of the present invention including the above-noted paraffin mixture may be used as a solid and liquid base used for, for example, cosmetics, cleansing oils, and pharmaceutical preparations for hair or skin.

[Volatile Oil for Hair Cosmetics]

The volatile oil for cosmetics of the present invention is used as a volatile oil for hair cosmetics for explanation.

When the volatile oil for cosmetics of the present invention is used for hair cosmetics, the content of the volatile oil for cosmetics may be properly selected. Particularly, in clearly showing the effects of the volatile oil for cosmetics of the present invention, for example, increasing volatility or improving dilution performance and compatibility of other cosmetic bases, the volatile oil for cosmetics of the present invention is blended in a hair cosmetic composition at 5 to 90 mass % or preferably 10 to 70 mass % although the blending quantity is different depending on its application purpose.

Hair cosmetics blended with the volatile oil for cosmetics of the present invention may contain an assistant and an additive, for example, a surfactant, more oil components, a moisturizer, a pearlescent wax, a viscous agent, a thickener, a superfatting agent, a stabilizer, a water-soluble and oil-soluble polymer, fat, wax, lecithin, phospholipid, a biogenic activate substance, an ultraviolet absorber, an ultraviolet scattering agent, organic and inorganic pigment, antioxidant, deodorant, a whitening agent, antiperspirant, hair tonic, a nonsteroidal antiinflammatory drug, blood circulation accelerator, dandruff inhibitor (remover), a film forming agent, a swelling agent, an insecticide, a tyrosinase inhibitor (depigmentation agent), hydrotrope, solubilizer, a preservative, balm, a coloring agent, a pH regulator, a chelating agent, etc.

Hair cosmetics blended with the volatile oil for cosmetics of the present invention may be applied in various agent forms and may be provided in the form of use of, for example, liquid, cream, emulsion, gel, mousse and so forth. It is useful to use them as a hair-setting product such as an aerosol hair spray, a pump type hair spray, a foam type hair spray, a hair mist setting lotion, a hair styling product, and hair oil, and a product with a conditioning property such as shampoo, conditioner, perm solution, and hair treatment.

These hair cosmetics may also be produced by emulsification or mixing. Emulsification or mixing may be carried out with an agitator such as a homogenizer, a homomixer, and a mill, or an agitator that applies another principle such as high pressure and ultrasonic waves.

[Volatile Oil for External Preparations for Skin]

The volatile oil for cosmetics of the present invention is used as a volatile oil for external preparations for skin for explanation.

When the volatile oil for cosmetics of the present invention is used for external preparations for skin, the content of the volatile oil for cosmetics may be appropriately selected. Particularly, in clearly showing the effects of the volatile oil for cosmetics of the present invention, for example, increasing volatility or improving dilution performance and compatibility of other cosmetic bases, the volatile oil for cosmetics of the present invention is blended in external preparations for skin (for example, cosmetics, cleansing oils, and pharmaceutical preparations for skin) at 3 to 90 mass % or preferably 10 to 70 mass % although the blending quantity is different depending on its application purpose.

External preparations for skin (for example, cosmetics, cleansing oils, and pharmaceutical preparations for skin) blended with the volatile oil for cosmetics of the present invention may contain an assistant and an additive, for example, a surfactant, more oil components, a moisturizer, a pearlescent wax, a viscous agent, a thickener, a superfatting agent, a stabilizer, a water-soluble and oil-soluble polymer, fat, wax, lecithin, phospholipid, a biogenic activate substance, an ultraviolet absorber, an ultraviolet scattering agent, organic and inorganic pigment, antioxidant, deodorant, a whitening agent, antiperspirant, a nonsteroidal anti-inflammatory drug, blood circulation accelerator, a film forming agent, a swelling agent, an insecticide, a preservative, a tyrosinase inhibitor (depigmentation agent), hydrotrope, solubiizer, a preservative, balm, a coloring agent, a pH regulator, and a chelating agent.

External preparations for skin (for example, cosmetics, cleansing oils, and pharmaceutical preparations for skin) blended with the volatile oil for cosmetics of the present invention may be applied in various agent forms and may be provided in the form of use of, for example, liquid, cream, emulsion, gel, mousse and so forth. It is useful to use them as skin lotion, skin cream, cleansing oil, cleansing cream, cleansing foam, cleansing gel, cleansing lotion, cleansing mask, beauty lotion, and beauty cream as well as ointment and spray.

These external preparations for skin may be also produced by emulsification or mixing. Emulsification or mixing may be carried out with an agitator such as a homogenizer, a homomixer, and a mill, or an agitator that applies another principle such as high pressure and ultrasonic waves.

EXAMPLES

The present invention will be explained in further detail below by referring to examples and comparative examples. Various physical properties in each example were measured by the following methods.

<Iodine Value>

Iodine values were determined in accordance with a test method of iodine value of JIS K0070.

<Boiling Point Range>

Boiling point ranges were determined in accordance with a determination of distillation characteristics of JIS K2254.

<Flash Point>

Flash points were determined in accordance with a determination of flash point by a closed cup method of JIS K2265.

<Number Average Molecular Weight>

A GPC (Gel Permeation Chromatography) measuring instrument from Shimadzu Corporation was used to measure number average molecular weights (in terms of polystyrene).

<Method of Analyzing Isododecane Contents>

With isododecane as a specimen, elution positions were confirmed with an analysis by a GC-14B Gas Chromatography from Shimadzu Corporation, and the content of a compound at the elution positions was measured.

Conditions of Gas Chromatography Analysis

Column: Nonpolar capillary column, 0.55 mm, 30 m, 5 μm

Temperature: 80° C. to 250° C.; Programmed temperature gas chromatography at 10° C./min.

Example 1

Through the following steps 1 to 4, the volatile oil for cosmetics including a paraffin mixture was produced.

360 g of a mixed gas, composed of an olefin mixed gas having a carbon number of 4 that contains 30 mass % of isobutylene, 18 mass % of 1-butene, and 25 mass % of 2-butene as well as the remaining 27 mass % of butane gas, was charged in an autoclave, and polymerization reaction was carried out under the existence of an aluminum chloride catalyst, thus providing a polymerization reaction system of isobutylene and normal butene.

(Step 1)

Unreacted gas in the autoclave after the reaction was removed by nitrogen gas substitution, and a polybutene mixture was extracted as a polymerization reaction mixture. Then, the catalyst was removed by a treatment with a caustic alkaline aqueous solution and by water rinse. Subsequently, the polybutene mixture that had been rinsed with water was charged in a 1 liter 4-neck flask and heated with an oil bath so as to remove an unreacted as component dissolved in the polybutene mixture by nitrogen bubbling at 40° C. of inner temperature, and was then treated with simple distillation at the inner temperature of 140° C. and the pressure reduction degree of 5 kPa. As a result, a polymer having a carbon number of 20 or more was left in the flask as a distillation residue, thus providing a polybutene mixture having a carbon number of 16 or less. The polybutene mixture had the number average molecular weight of about 185.

(Step 2)

Hydrogen was added to this polybutene mixture with 10 mass % of a hydrogenation catalyst (0.5% Pd carrying alumina catalyst) at 3 MPa of hydrogen pressure and 220° C. in the autoclave, thus providing 160 g of a paraffin mixture. The paraffin mixture had the iodine value of 0.1 and the number average molecular weight of about 180.

(Step 3)

Into a glass cylinder having 4 cm in outer diameter and 30 cm in length, attapulgus clay was first filled and then activated clay was filled at the volume ratio of 50:50, thus providing an adsorption column. The paraffin mixture provided in step 2 was continuously supplied from the bottom of the adsorption column at the flow velocity of 1 ml per minute and 25° C., and a trace metal compound originated from the catalyst and the apparatus material was adsorbed.

(Step 4)

At the bottom chamber of a 15-plate Oldershaw rectifying column, 150 g of the paraffin mixture was charged after the adsorption treatment in step 3, and was heated in an oil bath without exposure to air by bubbling dry nitrogen gas until the liquid temperature inside the chamber reached 110° C. When the liquid temperature inside the chamber reached 110° C., vacuum distillation was carried out for eight hours under decompression (10 kPa) at the reflux ratio of 10 and the distillation outflow temperature of 95° C., distilling 25 mass % of the whole charged quantity. Then, the dry nitrogen gas was again bubbled under decompression, thus cooling down liquid inside the bottom chamber and obtaining 112.5 g of a paraffin mixture. The content of 2,2,4,6,6-pentamethylheptane (isododecane) in the paraffin mixture was 2 mass %.

Example 2

The same procedure as in Example 1 was taken, except that 18% of a whole charged quantity was distilled in step 4, thus providing a volatile oil for cosmetics including 123 g of a paraffin mixture. The content of 2,2,4,6,6-pentamethylheptane (isododecane) in the paraffin mixture was 8 mass %. The boiling point range of this paraffin mixture was 185.0° C. to 212.1° C.

The volatile oil for cosmetics including a paraffin mixture obtained in Example 1 was compared with various conventional cosmetic oils having volatility in terms of boiling points, volatility, texture when applied to hair and texture when applied to skin, and the summary is shown in Table 1.

It is noted that for the order of volatility in Table 1, 0.1 g of each sample was spread on a filter paper of 110 mm in diameter, and the weight was measured after drying for two hours. Ranking was based on the order of the speed that it took the samples to be completely dry and 0 g in weight.

Sensory evaluation was made by 10 panelists to test the texture when applied to hair. In testing the texture when applied to hair, 1 g of a bundle of healthy Chinese hair was used. An appropriate amount of each sample was applied to the hair with hands.

Sensory evaluation was made by 10 panelists to test the texture when applied to skin.

TABLE 1

Comparative Evaluation of Various Cosmetic Oils

|  | Boiling Point (° C.) | order of volatility | texture when applied to hair | texture when applied to skin |
|---|---|---|---|---|
| volatile oil for cosmetics of Ex. 1 | 187.5-205 | 2 | light, silky smooth feeling continued, and hair styling is made easier | light, silky smooth feeling continued |
| Isododecane$^{(Remark\ 1)}$ | 177 | 1 | light but squeaky feel as evaporated | light, but applied part whitened as evaporated |
| cyclic silicone$^{(Note\ 2)}$ | 210 | 3 | feeling is smooth but not long-lasting when used alone | feeling is smooth but not long-lasting when used alone |
| Hydrogenated Polybutene$^{(Note\ 3)}$ | 220-250 | 4 | oily feeling remaining | oily feeling remaining |

$^{(Note\ 1)}$"MARUKASOL R" from Maruzen Petrochemical Co., Ltd. (Carbon number of 12; Flash point of 48° C.; Isododecane content of 95 mass % or more)
$^{(Note\ 2)}$"SH-245" from Dow Corning Toray Co., Ltd. (Flash point of 77° C.)
$^{(Note\ 3)}$Hydrogenated polybutene: PARLEAM 4 from NOF Corporation (Carbon number of 16; Boiling point range of 220° C. to 252.5° C.; Flash point of 88° C.; Isododecane content of 0 mass %)

As shown in Table 1, it was confirmed that the volatile oil for cosmetics of the present invention according to Example 1 not only had better volatility than cyclic silicones but also had excellent texture of oil itself and other properties shown below were also preferable.

[Volatile Oil for Hair Cosmetics]

Subsequently, various properties for hair of the volatile oil for cosmetics of the present invention were evaluated when they were used as a volatile oil for hair cosmetics.

With volatile oils for hair cosmetics including the paraffin mixture produced in Examples 1 and 2, the following various properties were evaluated in comparison with a blank with no oil treatment. As a comparison, cyclic silicone oil, isododecane, and hydrogenated polyisobutene were similarly evaluated, and the results are also shown in Table 2.

[Evaluation of Smoothness]

With the volatile oil for hair cosmetics of the present invention, coefficients of friction were measured by the method shown below, and the improvement of smoothness, when applied to hair, was evaluated.

Method of Evaluating Smoothness (Improvement after Treating Bleached Hair with Each Sample)

(Evaluation) MIU (Resistance: μ): Friction resistance of hair surface (Measuring Equipment) Friction tester (from Kato Tech Co., Ltd.)

(Measuring Conditions) Measurement environment at 20° C.; 40% of Humidity; Constant temperature and humidity chamber; Number of hair for measurement: ten; Contactor: Silicon rubber; Load: 25 gf (Hair Employed) Bleached healthy human hair that was purchased (Applying Various Oils and Preparing Tests)

(1) One hair is picked out of the bundle of human hair. Each sample is dropped onto an index finger cushion from a syringe, and is blended with a thumb.

(2) The picked hair is pinched between the index finger and the thumb, and is coated with a sample from its root to the end.

(3) After the sample is coated, excess sample is wiped off with a waste cloth made of paper (Trade Name: Kim Wipes). Ten oil-applied hairs, which are treated in much the same way, are arranged in a line with a 1 mm interval in between and are taped onto a slide glass for microscopy measurement with a double-sided tape, which is then used as a measurement sample.

(Assessment) With the coefficient of friction of hair untreated with oil as 100%, smoothness is evaluated after being treated with each sample. If there is an improvement in comparison with hair untreated with oil (blank), the number would be less than 100%.

[Hair Tensile Strength]

(Measuring Equipment) FUDOH RHEO METER RTC from Rheotech Co., Ltd.

(Measuring Condition) Measurement environment: Inside constant temperature chamber at 25° C.

(Hair Employed) Healthy Human Hair (Applying Various Oils and Preparing Tests)

Beforehand, a bundle of unbleached healthy hair for measurement is placed in a constant temperature chamber for one day.

(1) One hair is picked out of the bundle of human hair. Each sample is dropped onto an index finger cushion from a syringe, and is blended with a thumb.

(2) The picked hair is pinched between the index finger and the thumb, and is coated with a sample from its root to the end.

(3) After the sample is coated, excess oil is wiped off with a waste cloth made of paper (Trade Name: Kim Wipes).

(4) After ten human hairs are treated with each sample, hair diameter is measured with a diameter.

(5) The hair is fixed with a jag of an equipment, and is given a load by lowering a base onto which the hair is fixed.

(6) The load is recorded when the hair is broken by the load.

(Assessment) With the tensile strength of hair untreated with oil (blank) as 100%, tensile strength was evaluated after being treated with each sample. If there is an improvement in comparison with the blank, the number would be higher than 100%.

[Cuticle Repair Property]

(Measuring Equipment) Scanning microscope from JEOL Ltd., JSM-7400F (1) Each sample was dropped onto an index finger cushion by 0.1 cc and was blended with a thumb. One bleached hair was pinched between the index finger and the thumb, and was applied with the sample from its root towards the end. The same treatment was carried out to five hairs respectively.

(2) Excess oil was lightly wiped off and was washed off with distilled water. After one hour of drying, a certain procedure was taken for scanning electron microscopy measurement.

(Assessment) Observation was made at about 400 magnification to visually determine whether or not the cuticle was repaired.

If it was repaired, it was expressed as "o". If the repair was incomplete, "Δ" if no repair was recognized, "x", Method of Evaluating Smoothness (Improvement after Treating Skin with Each Sample)

(Evaluation) MIU (Resistance: μ): Friction resistance of skin surface (Measuring Equipment) Friction tester (from Kato Tech Co., Ltd.)

(Measuring Conditions) Measurement environment at 20° C.; 40% of Humidity; Constant temperature and humidity chamber; Measurement site: Inside upper arm; Contactor: Silicon rubber; Load: 25 gf (Applying Various Oils and Preparing Tests)

(1) The measurement site of a subject is washed with neutral detergent and tap water and then dried. The subject goes in the constant temperature and humidity chamber 30 min. before measurement to allow the measurement site to get used to the environment inside the chamber.

(2) Coefficients of friction at sites to be applied are measured before applying samples.

(3) Samples are dropped onto a measurement site by 10 μL with a micropipette, and are spread with a finger from an elbow towards a wrist in an area with the width of about 1.5

TABLE 2

Evaluation results of various hair characteristics

| Examples | No. | each sample treatment | smoothness (%) | tensile strength (%) | cuticle repair property |
|---|---|---|---|---|---|
| | | untreated with oil (blanks) | 100 | 100 | x |
| Example | 1 | volatile oil for hair cosmetics (content of 2,2,4,6,6-pentamethylheptane is 2 mass %) | 63 | 145 | o |
| | 2 | volatile oil for hair cosmetics (content of 2,2,4,6,6-pentamethylheptane is 8 mass %) | 62 | 140 | o |
| Comparative | 1 | cyclic silicone oil[Note 1] | 83 | 120 | Δ |
| Examples | 2 | Isododecane[Note 2] | 78 | 125 | Δ |
| | 3 | Hydrogenated Polybutene[Note 3] | 81 | 165 | o |

[Note 1]"SH-245" from Dow Corning Toray Co., Ltd. (Flash point of 77° C.)
[Note 2]"MARUKASOL R" from Maruzen Petrochemical Co., Ltd. (Carbon number of 12; Flash point of 48° C.; Isododecane content 95 mass % or more)
[Note 3]Hydrogenated polybutene: PARLEAM 4 from NOF Corporation (Carbon number of 16; Boiling point range of 220° C. to 252.5° C.; Flash point of 88° C.; Isododecane content of 0 mass %)

It is clear that the volatile oil for hair cosmetics of the present invention not only has excellent volatility and texture when applied to hair but also, according to evaluation results shown in Table 2, has better hair care properties, such as smoothness, tensile strength, and cuticle repair property, than various conventional oils for cosmetics. Accordingly, as the volatile oil for hair cosmetics of the present invention is blended in hair cosmetics, hair cosmetics with such excellent effects are provided.

[Volatile Oil for External Preparations for Skin]

Subsequently, various properties on skin were evaluated when the volatile oil for cosmetics of the present invention was used as a volatile oil for external preparations for skin.

With Volatile oils for external preparations for skin including the paraffin mixtures produced in Examples 1 and 2, the following various properties were evaluated in comparison with a blank with no oil treatment. As a comparison, cyclic silicone oil, isododecane, and hydrogenated polyisobutene were similarly evaluated, and the results are shown in Table 3.

[Evaluation of Smoothness]

With the volatile oil for external preparations for skin of the present invention, coefficients of friction were measured by the following method, and the improvement of smoothness when applied to skin was evaluated.

cm×the length of about 5 cm. Excess samples are wiped off with a waste cloth made of paper (Trade Name: Kim Wipes).

(4) After the samples are applied, the coefficients of friction at applied sites are measured every thirty minutes.

(Assessment) With the coefficient of friction at measurement sites before oil treatment as 100%, smoothness was evaluated after being treated with each sample. If there is an improvement in comparison with the ones untreated with oil (blanks), the number would be below 100%.

[Evaluation of Moisture Retention]

With the volatile oil for external preparations for skin of the present invention, the amount of moisture in a stratum corneum was measured by the method shown below, and the amount of moisture (moisture retention) was evaluated.

(Measuring Equipment) SKICON-200EX (from I.B.S. Co., Ltd.)

(Measuring Conditions) Temperature of 20° C., Humidity of 40%

(Testing Method) Samples are applied inside a human forearm, and the amount of moisture is measured after two hours.

(Applying Various Oils and Preparing Tests)

(1) The measurement site of a subject is washed with neutral detergent and tap water and then dried. The subject goes in the constant temperature and humidity chamber 30 min. before measurement to allow the measurement site to get used to the environment inside the chamber.

(2) Before applying samples, the amount of moisture is measured at a site to be applied that is marked in a circle 1 cm in diameter.

(3) Samples are dropped by 10 μL with a micropipette onto a measurement site that is marked in a circle with 1 cm in diameter, and are applied to skin at the marking site.

(4) The amount of moisture is measured at the measurement site two hours after being applied.

(Assessment) With the amount of water at measurement sites with no oil treatment (blanks) as 100%, the amount of moisture was evaluated after being treated with each sample. If there is an improvement in comparison with the blank, the number would be higher than 100%.

[Evaluation of Barrier Property]

With the volatile oil for external preparations for skin of the present invention, an evaporated water quantity in a stratum corneum was measured by the method shown below, and the evaporated water quantity (barrier property) was evaluated.

(Measuring Equipment) Tewameter™210 (from Courage+ Kahazaka Co., Ltd.)
(Measuring Conditions) Temperature of 20° C., Humidity of 40%
(Testing Method) Samples are applied inside a human forearm, and an evaporated water quantity is measured after two hours.
(Applying Various Oils and Preparing Tests)

(1) The measurement site of a subject is washed with neutral detergent and tap water and then dried. The subject goes in the constant temperature and humidity chamber 30 min. before measurement to allow the measurement site to get used to the environment inside the chamber.

(2) Before applying samples, an evaporated water quantity is measured at a site to be applied that is marked in a circle 1 cm in diameter.

(3) Samples are dropped by 10 μL with a micropipette onto a measurement site that is marked in a circle with 1 cm in diameter, and are applied to skin at the marking site.

(4) The evaporated water quantity is measured at the measurement site two hours after being applied.

(Assessment) With the evaporated water quantity at measurement sites with no oil treatment (blanks) as 100%, the evaporated water quantity was evaluated after being treated with each sample. If there is an improvement in comparison with the blanks, the number would be lower than 100%.

[Evaluation of Skin Viscoelasticity]

With the volatile oil for external preparations for skin of the present invention, skin viscoelasticity was measured by the method shown below, and the skin viscoelasticity was evaluated.

(Measuring Equipment) Cutometer (from I.B.S. Co., Ltd.)
(Measuring Conditions) Temperature of 20° C., Humidity of 40%
(Testing Method) Samples are applied inside a human forearm, and viscoelasticity is measured after two hours.
(Applying Various Oils and Preparing Tests)

(1) The measurement site of a subject is washed with neutral detergent and tap water and then dried. The subject goes in the constant temperature and humidity chamber 30 min. before measurement to allow the measurement site to get used to the environment inside the chamber.

(2) Before applying samples, viscoelasticity is measured at a site to be applied that is marked in a circle with 1 cm in diameter.

(3) Samples are dropped by 10 μL with a micropipette onto a measurement site that is marked in a circle with 1 cm in diameter, and are applied, to skin at the marking site.

(4) The viscoelasticity is measured at the measurement site two hours after being applied.

(Assessment) With the amount of moisture at measurement sites with no oil treatment (blanks) as 100%, skin viscoelasticity was evaluated after being treated with each sample. If there is an improvement in comparison with the blank, the number would be higher than 100%.

TABLE 3

Evaluation results of various skin characteristics

| Examples | No. | each sample treatment | smoothness (%) | water quantity in stratum corneum (%) | evaporated water quantity (%) | skin viscoelasticity (%) |
|---|---|---|---|---|---|---|
| | | untreated with oil (blanks) | 100 | 100 | 100 | 100 |
| Example | 1 | volatile oil for external preparations for skin (content of 2,2,4,6,6-pentamethylheptane is 2 mass %) | 78 | 180 | 90 | 110 |
| | 2 | volatile oil for external preparations for skin (content of 2,2,4,6,6-pentamethylheptane is 8 mass %) | 76 | 176 | 93 | 108 |
| Comparative | 1 | cyclic silicone oil[Note 1] | 108 | 120 | 106 | 95 |
| Examples | 2 | Isododecane[Note 2] | 104 | 112 | 105 | 97 |
| | 3 | Hydrogenated Polybutene[Note 3] | 116 | 144 | 94 | 99 |

[Note 1]"SH-245" from Dow Corning Toray Co., Ltd. (Flash point of 77° C.)
[Note 2]"MARUKASOL R" from Maruzen Petrochemical Co., Ltd. (Carbon number of 12; Flash point of 48° C.; Isododecane content of 95 mass % or more)
[Note 3]Hydrogenated polybutene: PARLEAM 4 from NOF Corporation (Carbon number of 16; Boiling point range of 220° C. to 252.5° C.; Flash point of 88° C.; Isododecane content of 0 mass %)

It is clear that the volatile oil for external preparations for skin of the present invention is not only excellent in volatility and texture when applied to skin but also, according to evaluation results shown in Table 3, is but also excellent in skincare properties, such as smoothness, moisture retention, barrier property, and skin viscoelasticity, than various conventional oils for external preparations. Thus, by blending the volatile oil for external preparations for skin of the present invention into external preparations for skin, there obtained are external preparations for skin having these excellent effects.

The invention claimed is:

1. A volatile oil for cosmetics comprising a paraffin mixture that contains isoparaffin having a carbon number of 12 to 16, has a boiling point range of 185° C. to 215° C., and contains 2, 2, 4, 6, 6-pentamethylheptane at less than 10 mass %, and does not contain nonvolatile hydrocarbon component.

2. The volatile oil for cosmetics according to claim 1, wherein use for the cosmetics includes use for hair cosmetics.

3. The volatile oil for cosmetics according to claim 1, wherein use for the cosmetics includes use for external preparations for skin.

4. A method of producing a volatile oil for cosmetics comprising a paraffin mixture that contains isoparaffin having a carbon number of 12 to 16, has a boiling point range of 185° C. to 215° C., and contains 2, 2, 4, 6, 6-pentamethylheptane at less than 10 mass %, comprising:

provided a polybutene mixture having a carbon number of 16 or less by removing unreacted isobutylene and normal butene and a polymer having a carbon number of 20 or more from a polymerization reaction system of isobutylene and normal butene;

providing a paraffin mixture having a carbon number of 16 or less by hydrogenating the polybutene mixture having a carbon number of 16 or less;

treating the paraffin mixture having a carbon number of 16 or less with an adsorbent so as to have an iron content of 10 ppm or less; and distilling the paraffin mixture having a carbon number of 16 or less that is treated with an adsorbent by 15 mass % or more with respect to a charged quantity by vacuum distillation.

* * * * *